(12) United States Patent
Waldock

(10) Patent No.: US 6,203,549 B1
(45) Date of Patent: Mar. 20, 2001

(54) INJECTORS FOR INTRAOCULAR LENSES

(75) Inventor: Terence Arnold Waldock, Meppershall (GB)

(73) Assignee: Duckworth & Kent Limited, Hertfordshire (GB)

(*) Notice: Subject to any disclaimer, the term of this patent is extended or adjusted under 35 U.S.C. 154(b) by 0 days.

(21) Appl. No.: 09/380,127

(22) PCT Filed: Dec. 29, 1998

(86) PCT No.: PCT/GB98/03917

§ 371 Date: Aug. 25, 1999

§ 102(e) Date: Aug. 25, 1999

(87) PCT Pub. No.: WO99/33411

PCT Pub. Date: Jul. 8, 1999

(30) Foreign Application Priority Data

Dec. 29, 1997 (GB) .................................................... 9727316
Jan. 22, 1998 (GB) .................................................... 9801214

(51) Int. Cl.⁷ ...................................................... A61F 9/00
(52) U.S. Cl. .............................................................. 606/107
(58) Field of Search .............................................. 606/107

(56) References Cited

U.S. PATENT DOCUMENTS

| | | | |
|---|---|---|---|
| 4,976,716 | 12/1990 | Cumming | 606/107 |
| 5,190,552 * | 3/1993 | Kelman | 606/107 |
| 5,620,450 | 4/1997 | Eagles et al. | 606/107 |
| 5,860,984 * | 1/1999 | Chambers et al. | 606/107 |
| 5,873,879 * | 2/1999 | Figueroa | 606/107 |
| 5,947,976 * | 9/1999 | Van Noy et al. | 606/107 |
| 6,001,107 * | 12/1999 | Feingold | 606/107 |
| 6,074,397 * | 6/2000 | Chambers et al. | 606/107 |

FOREIGN PATENT DOCUMENTS

WO 95/24863 9/1995 (WO).
WO 97/15253 5/1997 (WO).

* cited by examiner

*Primary Examiner*—Paul J. Hirsch
(74) *Attorney, Agent, or Firm*—Seidel, Gonda, Lavorgna & Monaco, PC

(57) ABSTRACT

An instrument for the insertion of an intraocular lens into an eye comprises a body portion, a nose portion through which runs a passage for the lens to pass to a dispensing tip, and a plunger. The nose portion is pivotally connected to the body portion so that the barrel can be broken open for the placement of the lens into the nose portion. The lens is preferably placed on two spaced parallel nose pins to facilitate its folding. A cross pin preferably straddles the nose pins and under which the lens is arranged to pass, to prevent lifting and tilting of the lens.

12 Claims, 13 Drawing Sheets

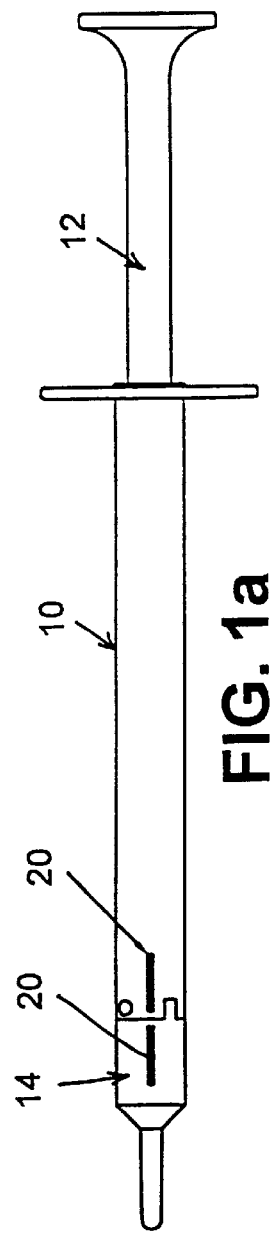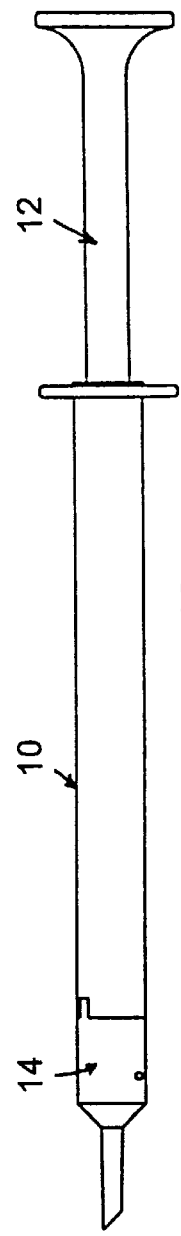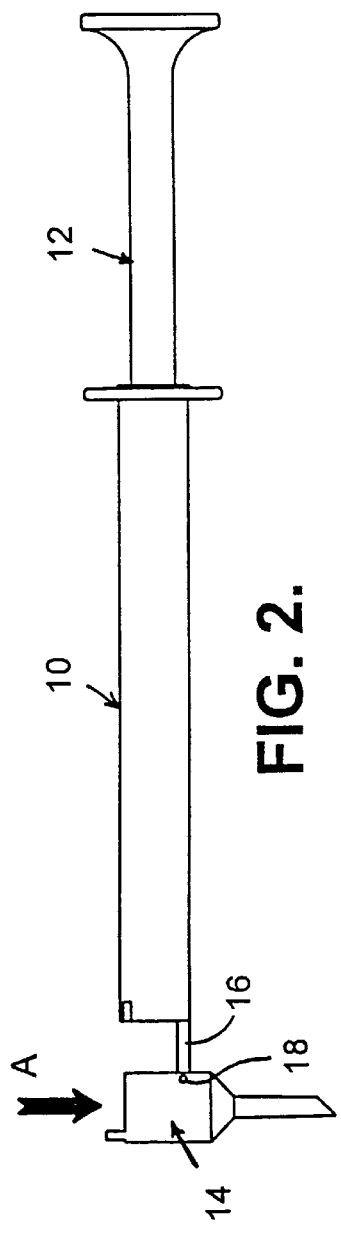

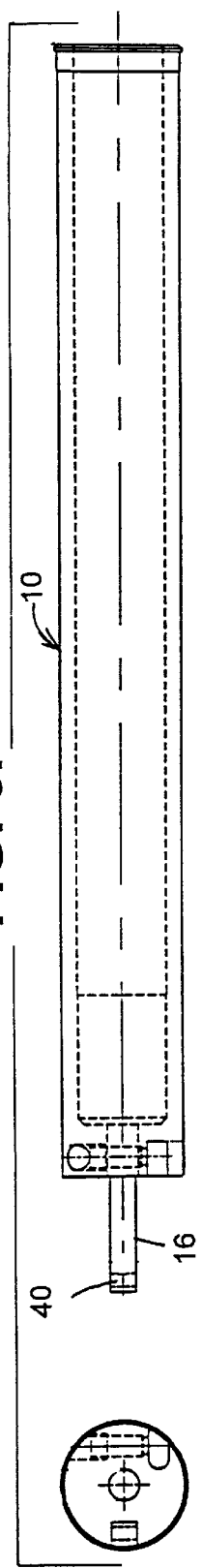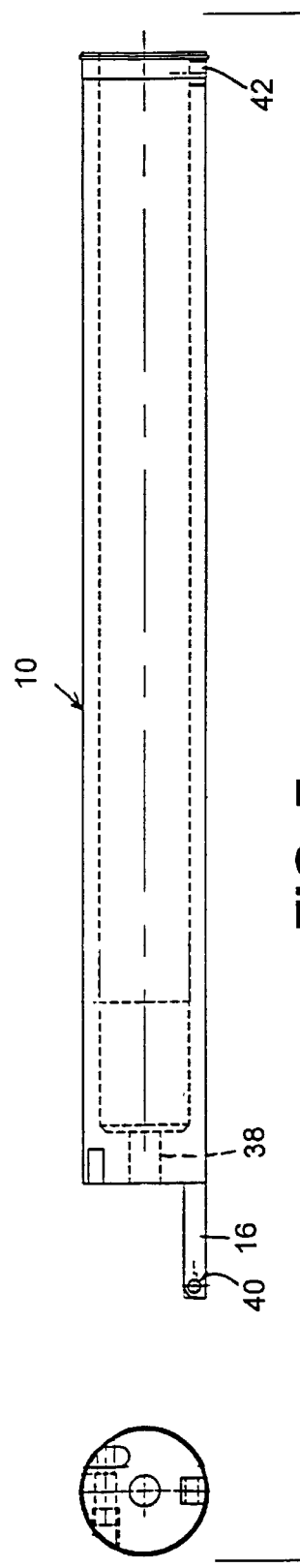

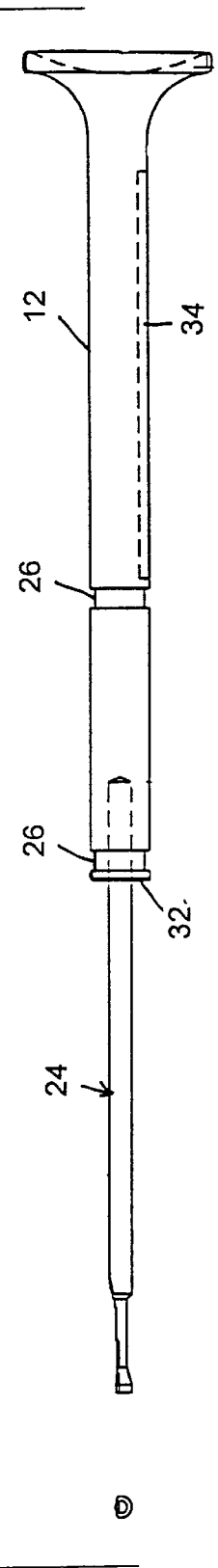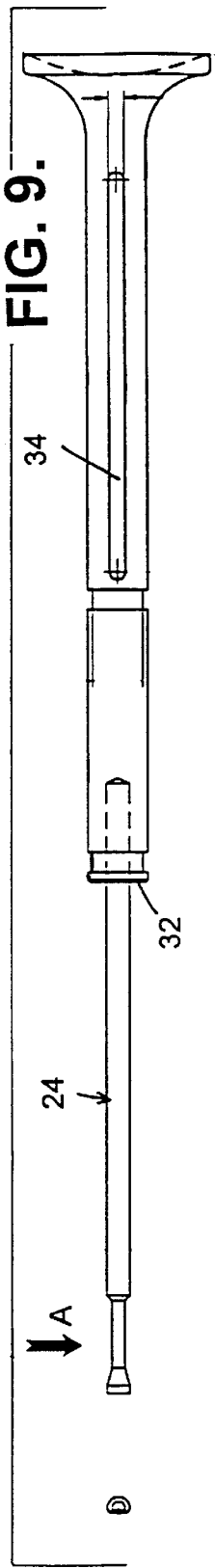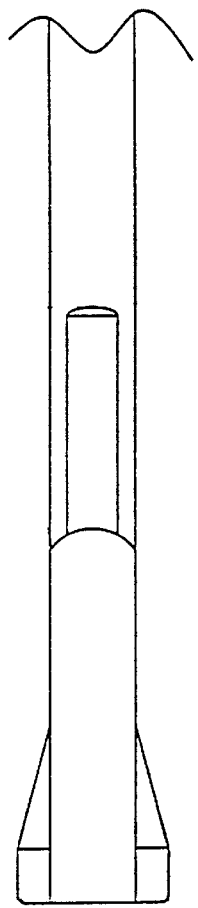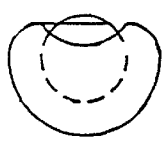

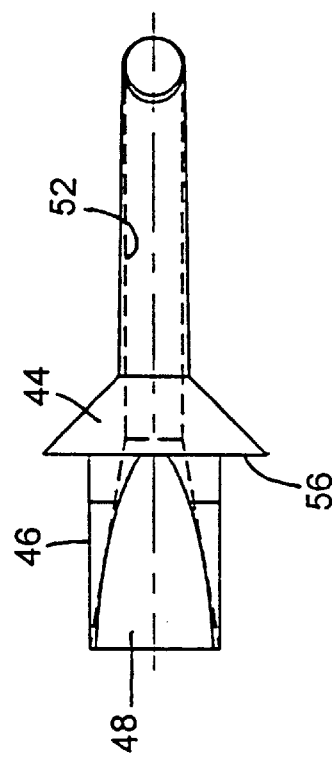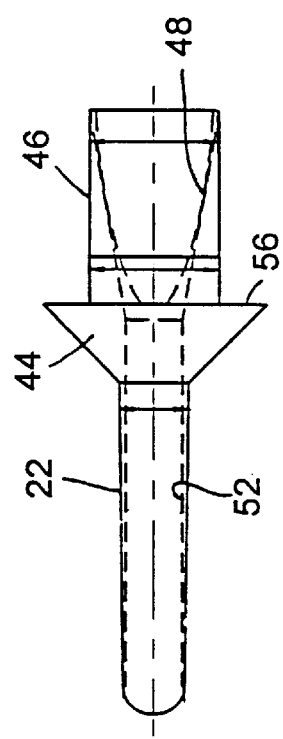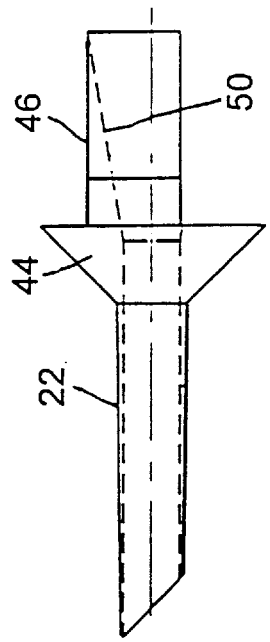

FIG. 18.
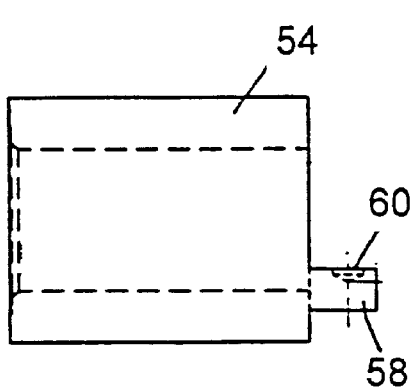
FIG. 20.
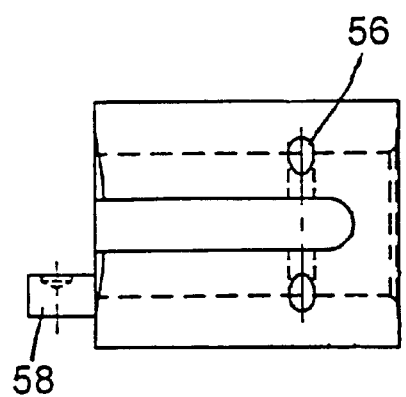
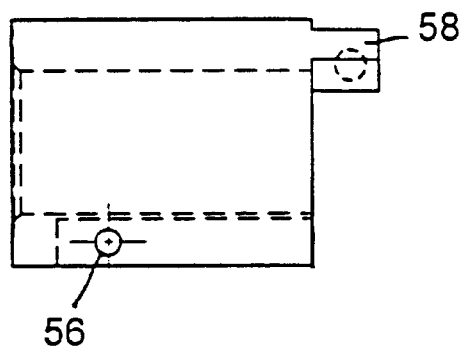
FIG. 19.

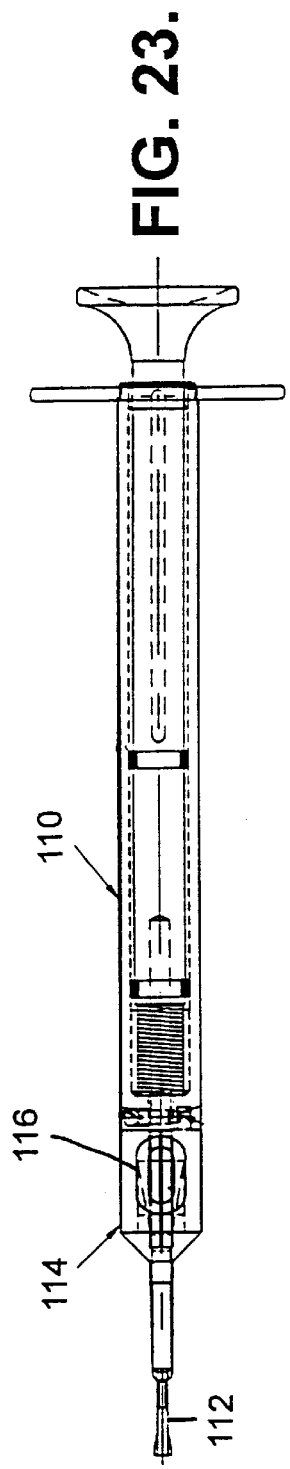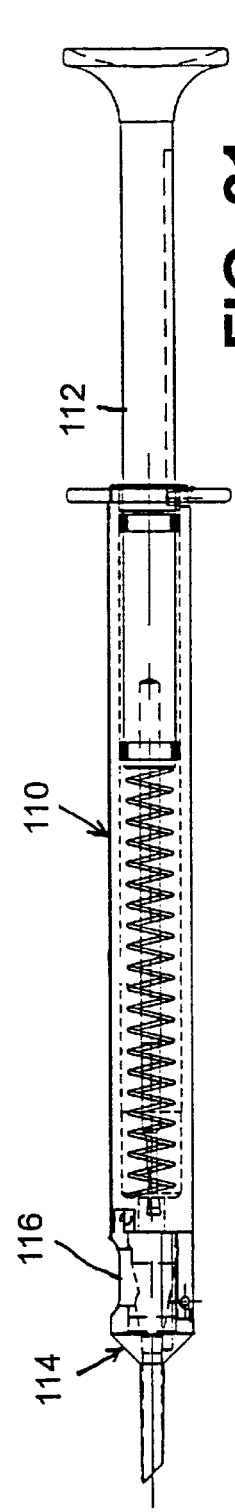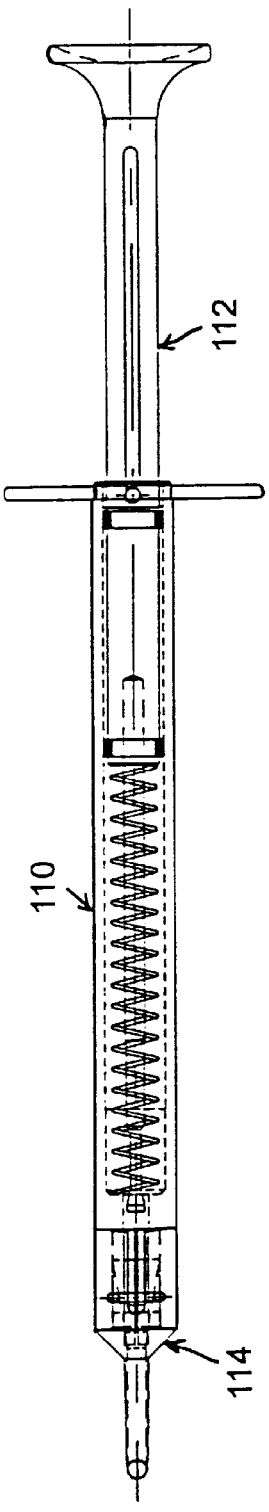

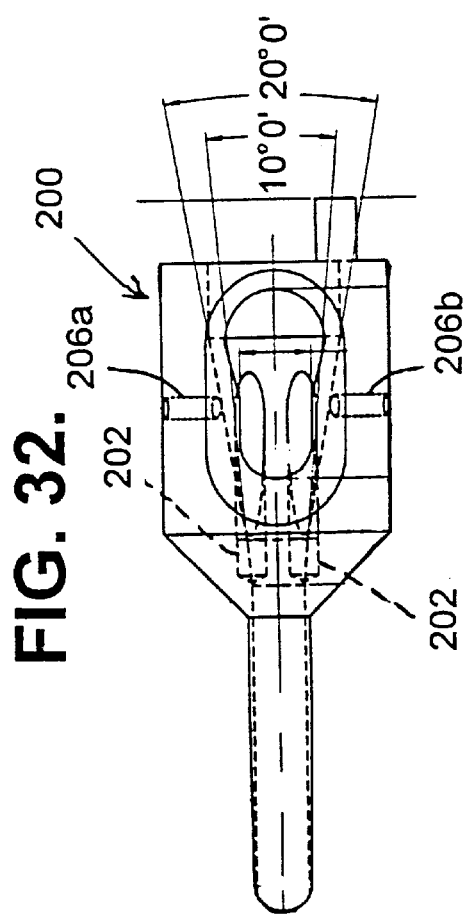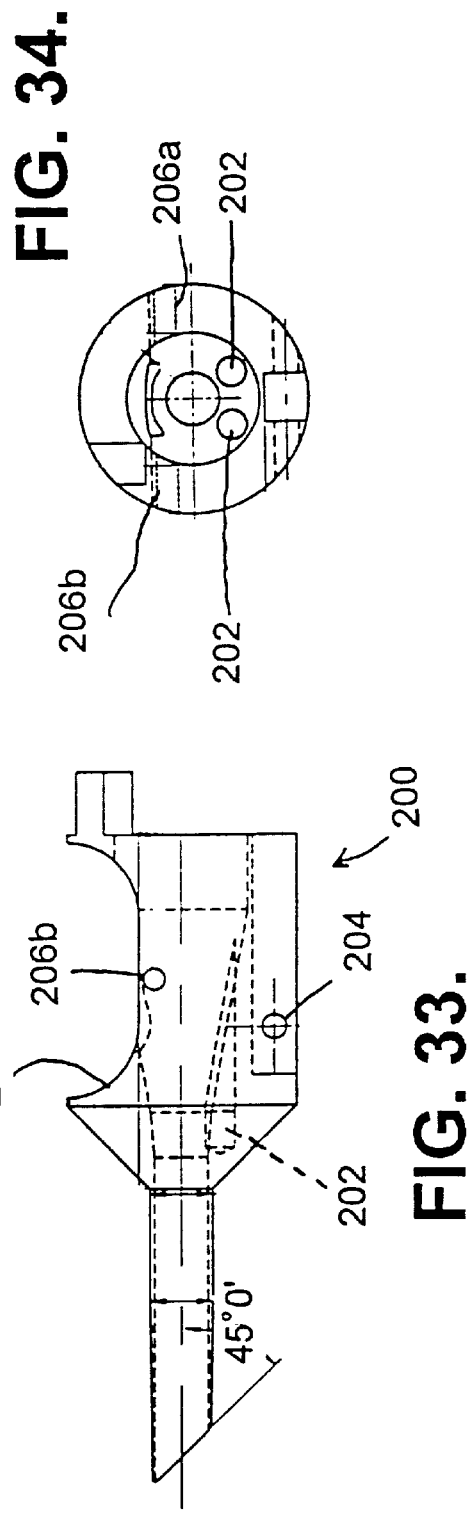

INJECTORS FOR INTRAOCULAR LENSES

This invention relates to instruments for inserting an intraocular lens into an eye. It is necessary in certain ophthalmic surgical procedures to insert an intraocular lens through a small incision, such as in the phacoemulsification technique of removing cataracts.

One particular instrument for carrying out this procedure is described in U.S. Pat. No. 4,681,102 (Bartell). In this instrument the intraocular lens is placed within a hinged, generally cylindrical load chamber having a pair of flanges. The load chamber is folded around the intraocular lens, so that the lens itself becomes folded or rolled along its length. The load chamber is fitted into an injector portion which has a slot which is keyed to the flanges of the load chamber. The injector portion and load chamber are then fitted into an insertion cone which defines a lumen for passage of the lens through the lumen. A plunger which is inserted into the injector portion is then used to push the lens through the lumen and into the eye. The folded intraocular lens opens out into its flattened form as it emerges from the distal end of the insertion cone.

In U.S. Pat. No. 4,681,102 the insertion cone, the load chamber and the injector portion are all separate pieces, preferably made of moulded plastics material, so that they can be disposed of after a single use. This means of course that there is a continuing expense in the use of the instrument and it is also necessary to have available a supply of parts.

It is an object of the present invention to provide an instrument for the insertion of intraocular lenses which does not involve the use of disposable parts.

It is a further object of the present invention to provide an instrument for the insertion of intraocular lenses in which the lens is not folded within a load chamber.

It is yet a further object of the present invention to provide an instrument for the insertion of intraocular lenses in which the lens can be placed easily into the instrument for subsequent injection.

The instrument of the present invention, dispensing as it does with disposable parts, is adapted for repeated use, with appropriate sterilisation, and can be made for example of titanium or a titanium alloy. One can produce an extremely accurately machined instrument which is easy both to load and to use.

In accordance with the present invention there is provided an instrument for the insertion of an intraocular lens into an eye, which comprises a body portion, a nose portion forward of the body portion and having a lumen through which the lens is arranged to pass, and a plunger movable through the body portion and the nose portion, wherein the nose portion is pivotally connected to the body portion for the receipt of an intraocular lens therein in a pivotally opened position.

Preferably, the nose portion is hingedly connected to the forward end of the body portion and is movable between open and closed positions in a manner similar to the opening and closing of a shotgun barrel. In the broken open position the lens can be inserted and then the nose portion is closed and locked into place for the operation then of the plunger to dispense the lens from the nose portion.

In a preferred embodiment, the lumen or internal channel through the nose portion reduces in cross-section in a smoothly continuous way so that as the lens passes deeper into the nose portion it is constrained to fold for dispensation through the tip of the nose portion.

According to a further preferred feature of the invention, the nose portion is pivotally mounted on a forward extension of the body portion, so that the hinge position is forward of the body portion and so that the nose portion, when in the open position, is spaced from the body portion to facilitate the placement of a lens into position in the nose.

It is a further object of the present invention to provide an instrument for the insertion of intraocular lenses in which the lens which is to be inserted is laid on support means which not only serves as a guide for the lens in its onward movement through the nose, but also facilitates the positioning of the lens correctly within the instrument.

In accordance with a preferred embodiment of the present invention there is provided an instrument for the insertion of an intraocular lens into an eye wherein there is provided support means for the lens which defines an undulating support surface for the lens.

Preferably, the support means comprises two parallel spaced nose pins whose surfaces define the undulating support surface for the lens.

The pins are preferably set into the rear end of the nose portion of the instrument.

The advantage of an undulating support surface for the lens, for example as provided by the two pins, is that this configuration also helps to centralise the forceps which are used to place the lens within the instrument. Additionally, the use of two spaced pins or an equivalent surface configuration helps to guide the lens into the funnel or lumen through which the lens has to pass. The space between the two pins, or the valley in some other equivalent configuration, allows the lens more easily to fold about its centre as it is pushed forward through the nose portion of the instrument.

Preferably the instrument includes a cross pin extending transversely across the path of the lens and beneath which the lens is arranged to pass. Preferably, the cross pin straddles the nose pins. The main purpose of the cross pin is to prevent lifting or tilting of the lens both on insertion into the nose and in its passage towards the tip.

In order that the invention may be more fully understood, a number of preferred embodiments of lens injector in accordance with the invention will now be described by way of example and with reference to the accompanying drawings. In the drawings:

FIG. 1*a* shows a plan view of a first embodiment of injector in accordance with the invention, in the closed position;

FIG. 1*b* is the side view of the injector of FIG. 1*a*;

FIG. 2 shows the injector according to FIG. 1*b*, but with the injector in the opened position;

FIG. 6 is a plan view of the main body of the lens injector;

FIG. 7 is the side view of the main body of the lens injector shown in FIG. 6;

FIG. 8 is a side view of the plunger and push rod of the lens injector;

FIG. 9 is the view of the plunger and push rod of FIG. 8, from below;

FIG. 10 is the view on arrow A in FIG. 9;

FIG. 11 is the front end view of the push rod, viewed from the left-hand end as shown in FIG. 10;

FIG. 15 shows the front portion of the nose assembly, in top plan view;

FIG. 16 shows the front portion of the nose assembly of FIG. 15, in side view;

FIG. 16a is the view on the right-hand end of FIG. 16;

FIG. 17 shows the front portion of the nose assembly of FIGS. 15 and 16, in underneath plan view;

FIGS. 18, 19 and 20 are plan, side and underneath plan views respectively of the outer sleeve which in combination with the front portion shown in FIGS. 15 to 17 forms the nose assembly shown in FIGS. 12 to 14;

FIG. 21 is a side view of a second embodiment of lens injector in accordance with the invention, with the plunger retracted;

FIG. 22 shows the lens injector of FIG. 21, but from below;

FIG. 23 is the top plan view of the lens injector of FIG. 21, with the plunger fully depressed;

FIG. 32 is the top plan view of a modified embodiment of nose assembly, illustrating the use of a cross pin in the lens passage;

FIG. 33 is the side view of the nose assembly of FIG. 32;

FIG. 34 is the end view of the nose assembly of FIGS. 32 and 33 taken from the right-hand end of FIG. 33;

Figure 3:
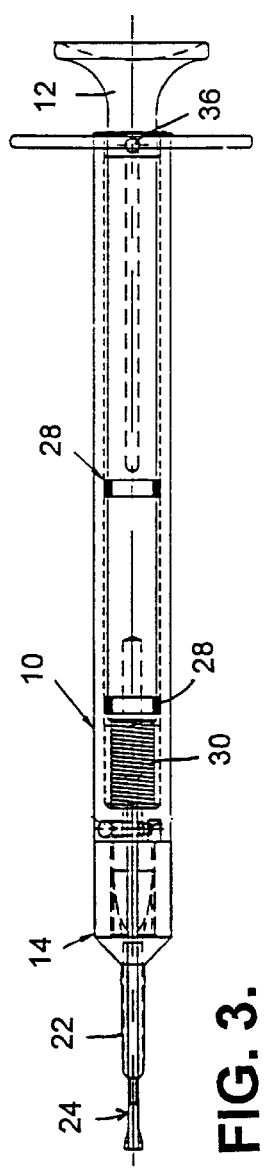
FIG. 3 shows internal details of the lens injector of FIGS. 1 and 2, and is shown with the plunger fully depressed.

A first embodiment of intraocular lens injector of the present invention is shown generally in FIGS. 1a, 1b and 2. It will be seen that the injector essentially comprises a body portion 10, a plunger 12 and a nose portion 14. Each of these parts will be described in more detail hereinafter. As will be apparent from these Figures, the nose portion 14 can be "broken open" in like manner to a shotgun barrel. In the closed position as shown in FIGS. 1a and 1b the nose portion 14 is coaxial with the main body 10 and the plunger 12. FIG. 2 shows the nose portion broken open. The body portion 10 has a finger 16 projecting from the front end of the body at the bottom of the body, and a pivot pin 18 extends through the nose portion and the finger 16 to provide the pivotal mounting. As shown in FIG. 2, the nose portion is pivotable through 90° from the open position to the closed position and vice versa. It will be seen in FIG. 1a that the nose portion and body portion are each provided with an engraved marking 20 with the markings being in alignment when the nose portion is closed. These lines provide an indication to the user as to where the nose portion should be pushed in order to open the nose.

Although the method of operation of the instrument will be described in more detail hereinafter, it will be helpful briefly to describe the method of use with reference to FIGS. 1a, 1b and 2. From the closed position shown in FIGS. 1a and 1b the injector is opened by holding the instrument with the engraved lines 20 uppermost and pushing down on the nose 14. With the nose portion thus opened, the intraocular lens to be inserted into the eye is placed into the nose in the direction of the arrow A in FIG. 2, using suitable forceps. The lens is slid forward on the flat face at the bottom of the nose, as will become evident from the later drawings of this embodiment. In the case of a haptic lens, when the rear haptic is fully into the nose, the nose is closed until it clicks shut. The plunger is then depressed, causing the lens to be ejected from the tip of the nose portion and through the incision in the eye.

Figure 4:
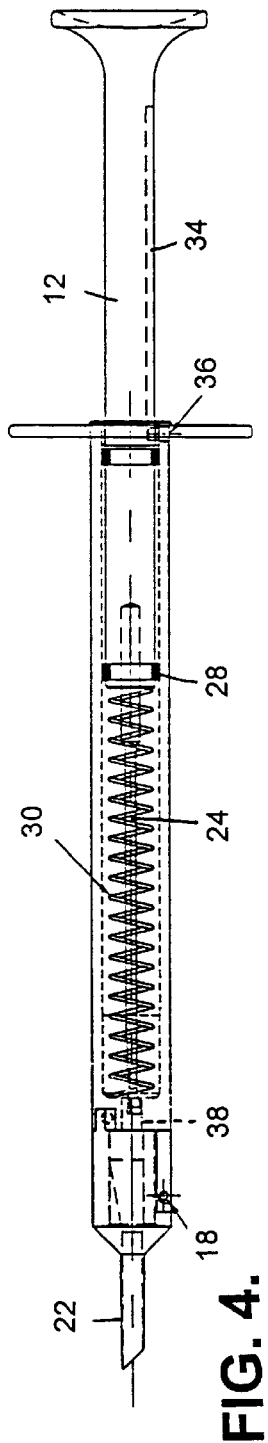
FIG. 4 shows the lens injector of FIG. 3, in side view, and with the plunger retracted.
Figure 5:
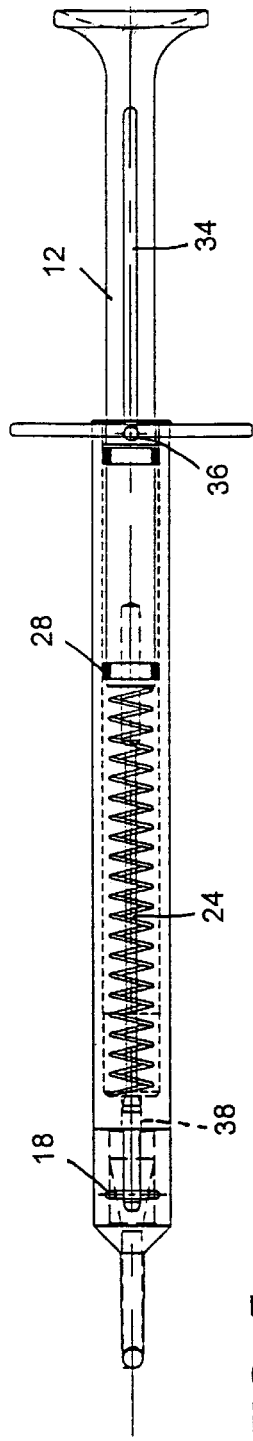
FIG. 5 shows the lens injector of FIG. 4, but from below.

Reference is now made to FIGS. 3 to 5, which show more details of the lens injector. The nose portion 14 will be described in more detail hereinafter. Suffice it to say here that there is a passage completely through the nose portion which changes in cross-section and configuration from one end of the nose portion to the other. At the distal end the nose portion has a tip 22 through which the lens is ejected. As shown in FIG. 3, when the plunger 12 is fully depressed, the push rod 24 passes out through the tip of the nose portion. The plunger 12 is slidable within the body portion 10 which is in the form of a cylindrical barrel having a bore therethrough. At two positions along its length the plunger 12 has circumferential grooves 26 (FIG. 8) which carry bushes 28 which have the purpose of steadying the plunger 12 as it is moved slidably within the barrel. A spring 30 provides a force against which the plunger is depressed and urges the plunger 12 into its retracted position. The spring 30 is seated at one end against an annular face inside the front end of the barrel and at the other end against a forwardly facing annular surface 32 (FIG. 8) at the forward end of the plunger 12. The underside of the plunger 12 is provided with a longitudinally extending groove 34. A stop pin 36 which extends radially through the wall of the body portion 10 at its rearward end projects into the groove 34 in the plunger 12 and serves as a stop to limit movement of the plunger both forwards and rearwards.

The push rod which is indicated generally at 24 is fitted into the forward end of the plunger 12. A hole is drilled in the plunger and the push rod is held in position by friction welding. The push rod 24 is of such a length that when the plunger 12 is fully retracted, as shown in FIGS. 4 and 5, the leading end of the push rod lies within the forward end of the body portion 10 and rearwardly of the nose portion 14. This enables the nose portion 14 to be broken open without danger of striking against the end of the push rod. As shown most clearly in FIG. 4, the leading end of the push rod 24 is located at the bottom of a counterbore 38 through the forward end of the body portion 10. Referring now to FIGS. 6 and 7, these show the body portion 10 in more detail. In particular, they show the forwardly projecting finger 16 at the leading end of the barrel and which is provided with a hole 40 therethrough to receive the pivot pin 18. At the rear end of the barrel, in FIG. 7, is shown a hole 42 into which the stop pin 36 is fitted.

FIGS. 8 to 11 show more details of the plunger 12 and push rod 24. The leading end of the push rod 24 is specially shaped, as shown most clearly in FIGS. 10 and 11, in order to enable the lens to be folded and pushed reliably and effectively through the nose portion and into the eye. The lens injector of the present invention can be used both with plate-type lenses and with haptic lenses. The shape of the push rod at its leading end is designed so that it will slide through the lumen in the nose portion 14 by virtue of its curved undersurface and yet will safely guide the lens through the lumen.

Figure 14:
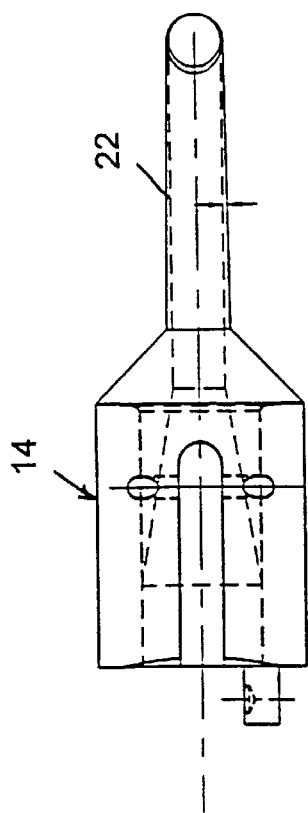
FIG. 14 is the underneath plan view of the nose assembly shown in FIGS. 12 and 13.
Figure 12:
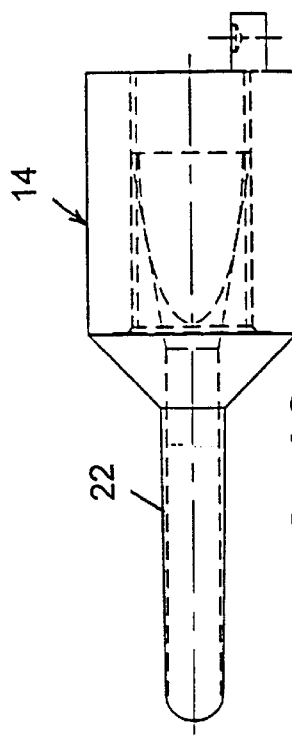
FIG. 12 is a plan view of the two-part nose assembly of the lens injector.
Figure 13:
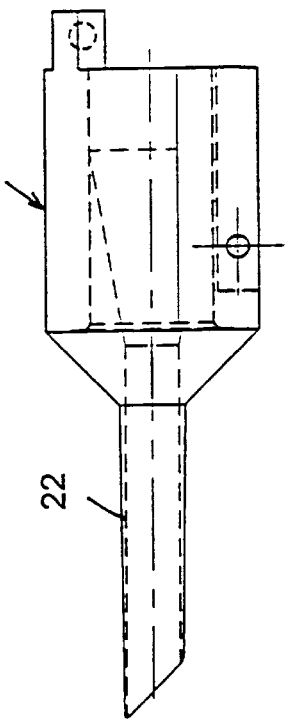
FIG. 13 is the side view of the nose assembly shown in FIG. 12.

FIGS. 12 to 14 show details of the nose assembly which is indicated generally at 14. The nose assembly is made in two parts, a front piece which is shown in FIGS. 15 to 17 and an outer sleeve which is shown in FIGS. 18 to 20. The front portion shown in FIGS. 15 to 17 includes the tip 22 which is cut off at 45° at the distal end. Behind the generally cylindrical but slightly tapering tip 22 is a frusto-conical portion 44. To the rear of that is a shaped portion 46 which includes a "bullet-shaped" recess 48 and a tapered bore indicated at 50 in FIG. 16. Shaping the rear portion 46 in this way causes the lens which is inserted here to be folded as it is pushed forward by the push rod into the cylindrical passage 52 through the tip 22. The folding of the lens is effected solely by the shape of the encircling passageway and only begins when the lens begins its movement through the nose portion.

The outer sleeve shown in FIGS. 18 to 20 comprises a generally cylindrical sleeve 54 which fits over the rear portion 46 of the front piece of the nose and which abuts the annular rearwardly facing surface 56 of the frusto-conical portion 44. The outer sleeve 54 is provided with a hole 56 therethrough which receives the pivot pin 18. The rearward end of the sleeve 54 is provided with a rearwardly projecting spigot 58 which is recessed as indicated at 60 to serve as a latch for a locking pin when the nose portion is closed against the body portion.

The whole instrument which comprises the lens injector is preferably made of titanium or a titanium alloy. This material can be machined to great accuracy and with a good surface finish. It can also be easily sterilised for repeated use.

The injector shown in FIGS. 21 to 31 essentially comprises a body portion 110, a plunger 112 and a nose portion 114. The nose portion 114 can be "broken open" in like manner to a shotgun barrel, as described in the preceding embodiment. In the closed position, as shown in FIGS. 21 to 23, the nose portion 114 is coaxial with the main body 110 and the plunger 112. As will be described in more detail hereinafter, with the plunger 112 retracted as shown in FIGS. 21 and 22, the nose portion 114 is broken open and the lens which is to be inserted into the eye is placed in the nose, using suitable forceps. In the present embodiment, the lens is inserted into the open rear end of the nose portion of the injector, using suitable forceps. The nose is then closed until it clicks shut. Subsequently the plunger is depressed, causing the lens to be ejected from the tip of the nose portion and through an incision in the eye.

In the present embodiment, the nose portion 114 is provided with a "window" 116 which is open to the chamber into which the lens is placed. This is simply a viewing window which enables the surgeon to see the lens in place. It also enables the surgeon to check that the rear haptic of an intraocular lens which has haptics is not caught by the front end of the plunger 112.

Figure 26:
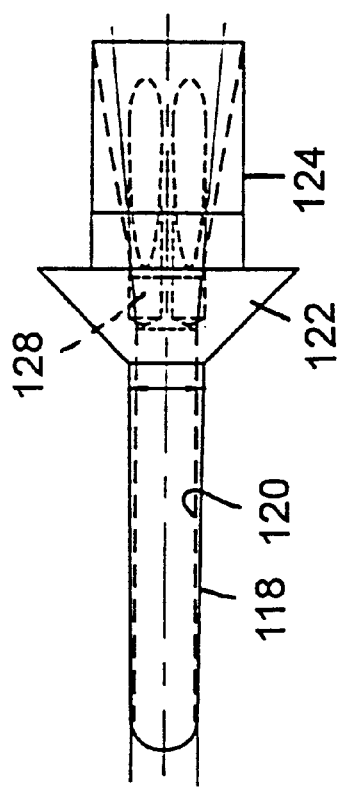
FIG. 26 is the plan view of the front piece of the nose portion shown in FIG. 24.
Figure 25:
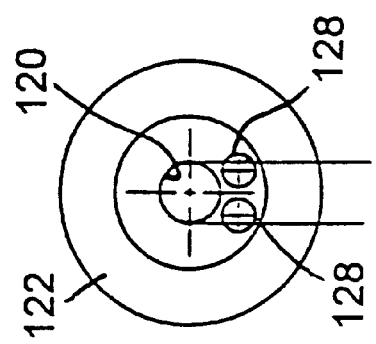
FIG. 25 is the end view taken in the direction of the arrow XXV in FIG. 24.
Figure 24:
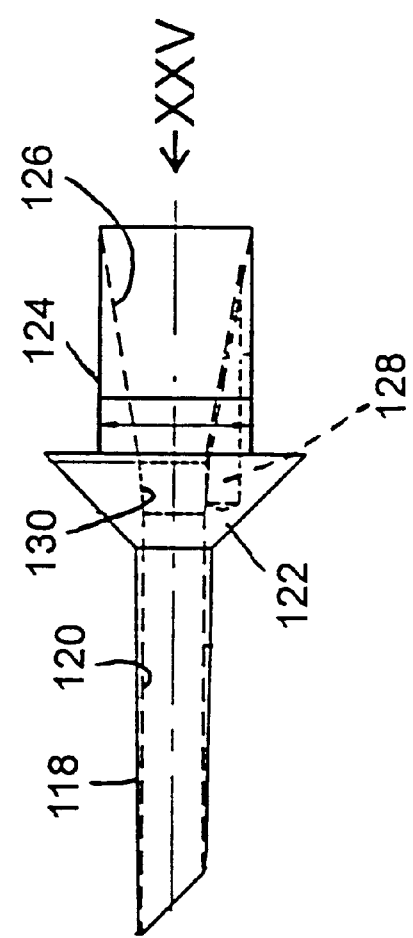
FIG. 24 is the side view of the front piece of the nose portion of the lens injector.
Figure 30:
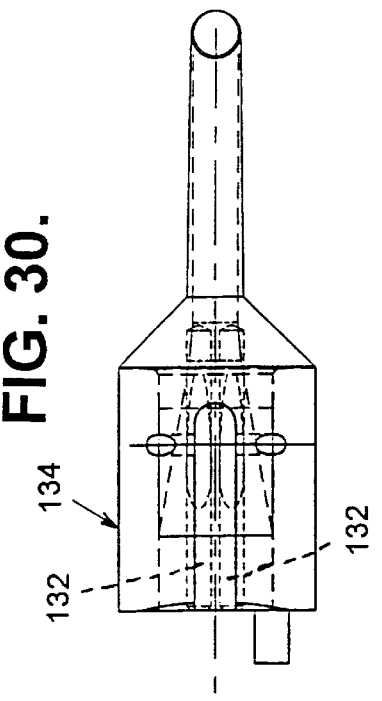
FIG. 30 is the underneath plan view of the nose assembly shown in FIG. 27.

Reference is now made to FIGS. 24 to 26, which show more details of the front piece of the nose assembly. The nose assembly is made in two parts, a front piece which is shown in FIGS. 24 to 26, and an outer sleeve which is shown in combination with the front portion in FIGS. 27 to 30. The front piece shown in FIGS. 24 to 26 includes a tip 118 which is cut off at 45° at the distal end. The tip has a cylindrical internal bore 120 of for example 2.2 mm diameter, with the external surface being generally cylindrical but slightly tapering. To the rear of the tip 18 is a frusto-conical portion 122. To the rear of that is a stub portion 124 which has a cylindrical external surface. The stub portion 124 has an internal tapered bore 126 which decreases in diameter from the rearward end towards the internal bore 120 in the tip 118. The bore 126 and the bore 120 together form a passage which is of decreasing cross-section from rearward end to forward end, but which is of circular cross-section throughout.

As shown in FIGS. 24 to 26, a pair of cylindrical holes 128 are bored into the stub portion 124 and frusto-conical portion 122 of the nose. These bores 128 extend parallel to the longitudinal axis of the nose portion. The forward end of each bore 128 lies approximately halfway along the length of the frusto-conical portion 122 and is contiguous at its periphery with the bore through the nose portion. The rearward end of each hole 128 exits in the sloping surface of the tapered bore 126.

As will be seen most clearly from FIG. 24, there is a transition zone in the internal bore, between the rearward tapering bore 126 and the forward cylindrical bore 120, within the frusto-conical portion 122. This transition bore 130 is tapered, but with a lesser taper than that of the rearward bore 126. The front end of each of the holes 128 "merges" with this transitional bore 130.

Figure 31:
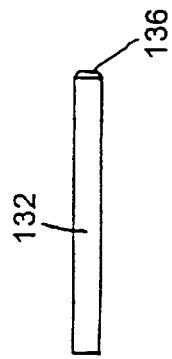
FIG. 31 shows one of the pins used in the nose assembly.
Figure 28:
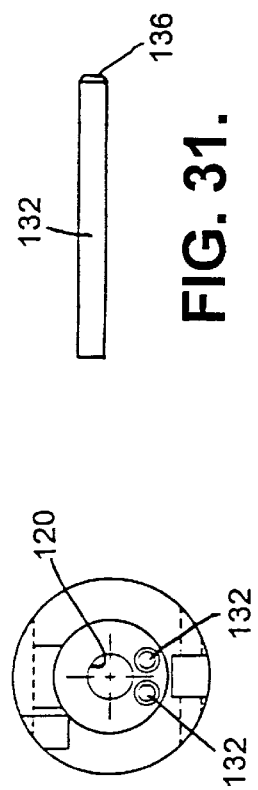
FIG. 28 is the end view taken in the direction of the arrow XXVIII in FIG. 27.
Figure 29:
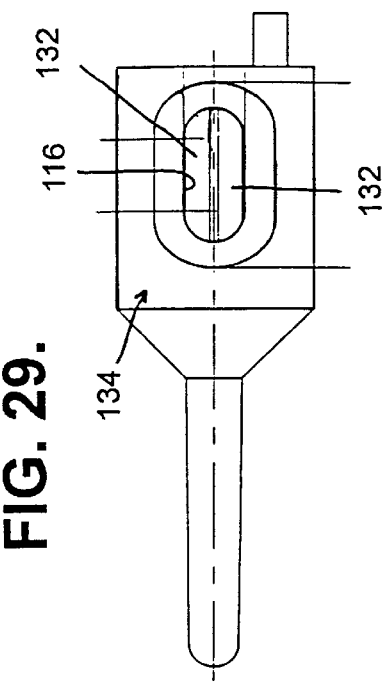
FIG. 29 is the top plan view of the nose assembly of FIG. 27.
Figure 27:
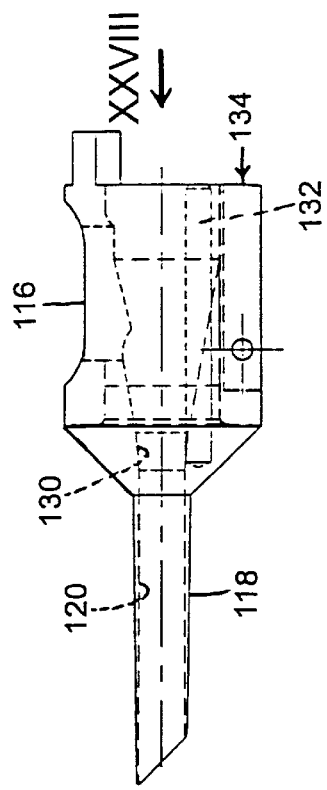
FIG. 27 is the side view of the complete nose assembly of the nose injector, including an outer sleeve.
Figure 36:
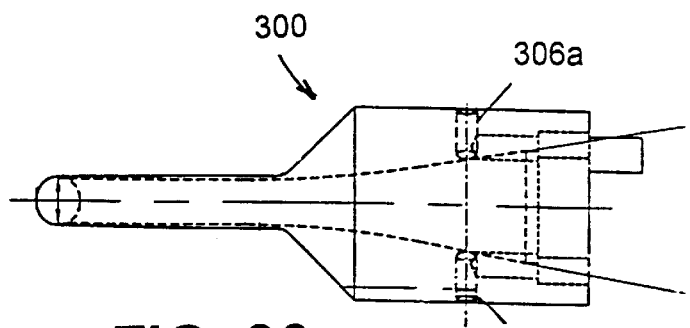
FIG. 36 is the top plan view of the nose of FIG. 35.
Figure 35:
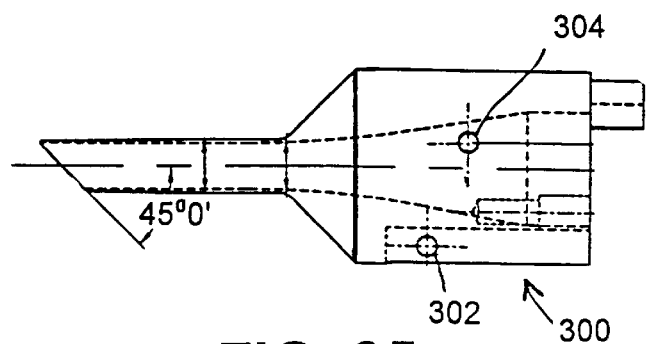
FIG. 35 is the side view of an alternative embodiment of nose for a lens injector according to the invention.
Figure 37:
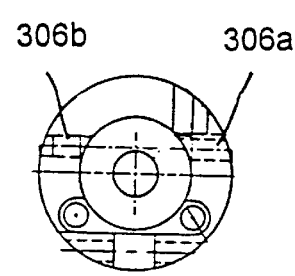
FIG. 37 is the end view of the nose of FIG. 35 taken from the right-hand end of FIG. 35.
Figure 38:
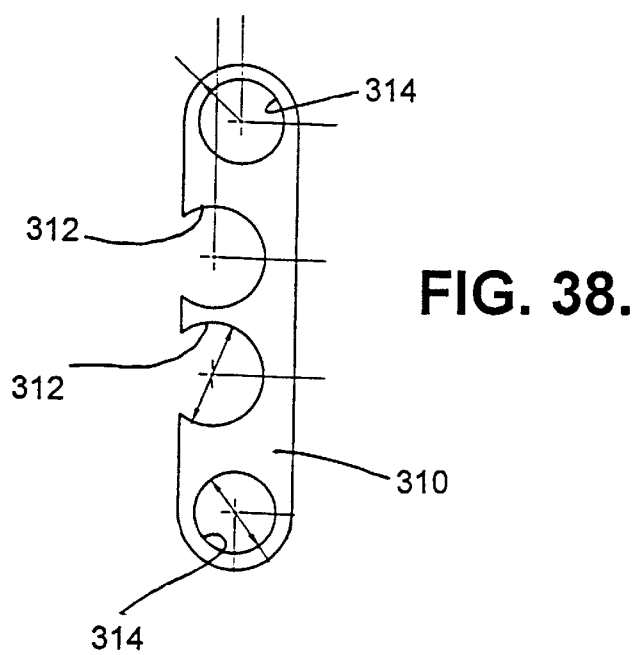
FIG. 38 shows the pin support which is fitted into the rear end of the nose of FIGS. 35 to 37.
Figure 39:
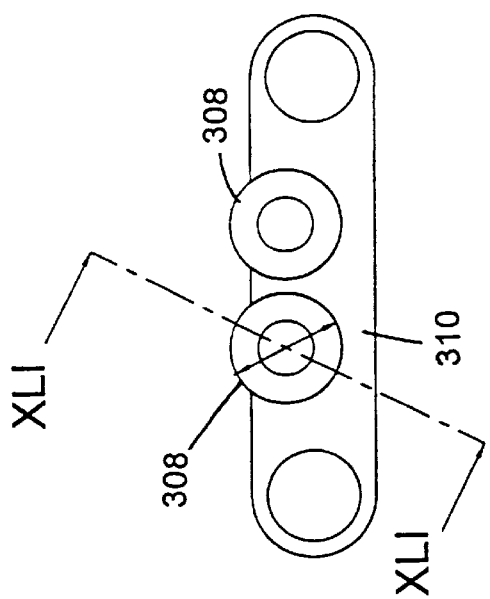
FIG. 39 shows the pin support of FIG. 38 fitted with two nose pins to make a nose pin assembly.
Figure 40:
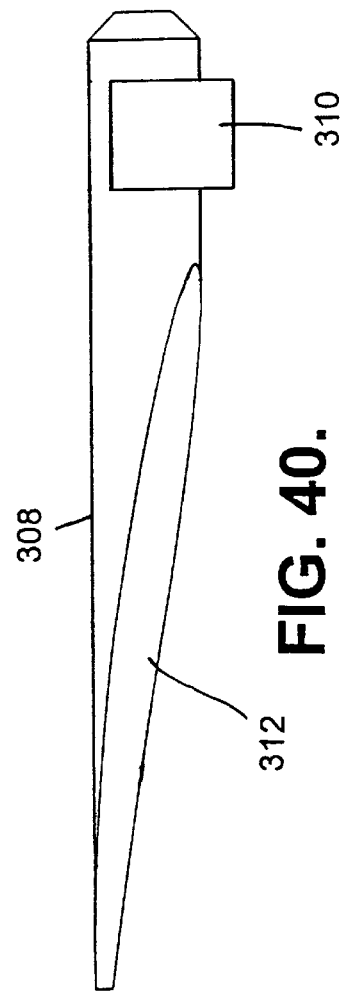
FIG. 40 is a side view of the nose pin assembly of FIG. 39.
Figure 41:
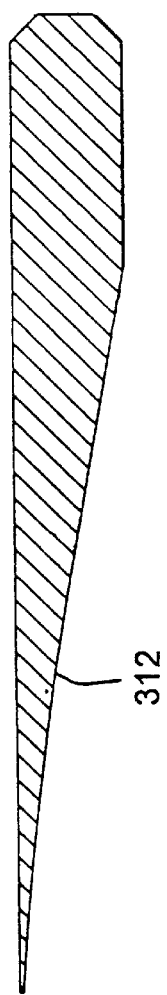
FIG. 41 is the sectional view on XLI—XLI in FIG. 39.

As will be seen from FIGS. 25 and 26, the two holes 128 are spaced apart, each at the same distance from the central vertical plane through the nose portion. They are thus symmetrically positioned in relation to the throughbore 126, 130, 120. Each of the holes 128 shown in FIGS. 24 to 26 is fitted with a cylindrical pin 132 which is shown in FIG. 31. Each pin 132 is cylindrical but has a chamfered rear end 136. A pin 132 is press-fitted into each of the holes 128 in the front piece of the nose portion. The rear end of each pin 132, when fitted, lies flush with the rearward end of the stub portion 124 of the front piece of the nose assembly. This is shown most clearly in FIGS. 27 to 30, which show the complete nose assembly consisting of the front piece, the two pins 132 and an outer sleeve 134 which is a press fit over the stub portion 124 of the front piece. The forward end of the sleeve 134 abuts the rearward end face of the frusto-conical portion 122. The outer sleeve 134 is provided with the window 116. This is dimensioned so that in use, as shown most clearly in FIG. 29, the two pins 132 can be seen in their side-by-side position below the window. The pivotal connection of the nose portion to the body portion of the instrument has been described earlier and is not repeated here.

In use, the intraocular lens which is to be inserted into the eye, whether with or without haptics, is inserted into the nose portion of the injector by first pivoting open the nose assembly and then inserting the lens, using forceps, from the rear end of the nose assembly through the open aperture which is there. Using the forceps, the lens is laid upon the two pins 132 in a sufficiently forward position that the rear haptic of the lens is forward of the rearward end of the nose assembly, so that it does not become caught when the nose assembly is closed to the main body. The provision of the two spaced pins 132 lends itself to the use of forceps to insert the lens. By using a pair of forceps which are essentially T-shaped in cross-section, the stem of the T can be slid between the two pins which will automatically centre the forceps within the chamber and guide the forceps and the lens forward until the lens is released and the forceps are withdrawn. This facilitates the insertion of the lens into the chamber.

In use, the intraocular lens is placed on the upper surface of the two pins. It is therefore supported on the two arcuate surfaces. When the lens is to be injected, the plunger 112 is depressed and the forward end of the plunger enters the chamber in the nose assembly at the level which enables it to slide forward over the pins 132, pushing the lens forward as it travels. As the lens passes forward through the bores 126, 130, 120, so it will be folded by the shape of the encircling circular cross-section passageway. The two pins 132 guide the lens while it passes through the tapering bores 126 and 130, and only terminate their guiding function when the lens enters the cylindrical bore 120 in the tip 118. A further feature of this arrangement is that because of the spacing of the two pins 132, with what is effectively a valley between them, as the lens is folded by the encircling walls, this folding is enhanced by a tendency for the central zone of the lens to sink into the valley between the pins and thus to ensure that the folding is symmetrical about the centre.

The whole instrument which comprises the lens injector is preferably made of titanium or a titanium alloy. This material can be machined to great accuracy and with a good surface finish. It can also be easily sterilised for repeated use. There are no disposable parts involved. The use of pins 132 is not a problem with a metal instrument, such as one made of titanium. It simply requires two holes to be bored in the nose piece and for the pins then to be fitted before the rest of the nose is assembled. This does not involve any complicated machining operations. However, particularly if alternative materials are used for the instrument, one could replace the pins by an internal configuration for the chamber within the nose assembly which is undulating and shaped to give the guiding and folding functions described above. For example, the lower portion of the internal chamber could be of undulating shape defining two arcuate peaks upon which the lens would be seated, in a manner analogous to that of the two pins 132.

Various alternative means of achieving the same functions as described above will be apparent to those skilled in this art. For example, instead of fitting pins into drilled holes in the nose assembly one could provide a suitably shaped insert arranged to be fitted into the chamber, with this insert again having a suitable seating surface configuration to provide the positioning and guiding functions described above. However, it has been found that the use of pins is a simple yet effective way of achieving the objects of the invention, particularly with a lens injector which is designed for repeated use.

Referring now to FIGS. 32 to 34, these show a modification of the nose, which can be used with any of the embodiments of the invention. The nose assembly 200 is here shown without the two nose pins, shown in FIGS. 27 to 30, although bores 202 for the nose pins are shown. The pivot pin for the pivoting of the nose assembly is here shown at 204. In this embodiment a pair of bores 206a, 206b are provided through the nose substantially midway along the length of the window 208 to receive a cross pin 210 which when fitted extends transversely across the direction of travel of the lens and at right-angles to the nose pins. The cross pin 210 is positioned straddling the nose pins so that when the lens is set in place using forceps the lens rests on the nose pins with its front edge under the cross pin. When the lens is pushed in under the cross pin, using the forceps, this starts the lens folding process. The cross pin 210 also prevents any possibility of the lens rising or tilting when it is inserted. Specially designed forceps can be used so that when the forceps strike the cross pin the user knows that the lens is correctly positioned and can be released.

After the lens has been set in place, the nose portion is pivoted into its closed position and the plunger can be operated to engage the lens and push it forwards, folding as it advances. The plunger is arranged just to pass beneath the cross pin 210 in its forward movement.

A further advantage of the use of two nose pins is that when using a lens having two haptics, the rear haptic drops down below the adjacent nose pin and therefore is never in the line of movement of the plunger and cannot become caught up by the plunger. This means that the double nose pin arrangement works much better than using a flat receiving plate or other surface for this lens.

FIGS. 35 to 41 show yet a further modification to the nose of the lens injector. The nose indicated generally at 300 is of generally the same configuration as those described earlier. It includes a pivot pin 302 to enable the barrel to be broken open. In this embodiment however there is no viewing window as in some earlier embodiments. There is however a cross pin 304 which is rivetted into a pair of bores 306a, 306b. In this embodiment, instead of fitting the two nose pins into holes drilled in the material of the nose, the nose pins 308 are carried by a pin support 310 which is itself fitted into the rear of the nose. The pin support 310 has two arcuate recesses 312 into which the nose pins 308 are seated. The pin support 310 also has two bores 314 adjacent to its respective ends, to enable it to be retained in the nose. As shown most clearly in FIGS. 39 and 40, the nose pins 308 rest proud of the surface of the pin support 310 to enable the lens to be deposited thereon. The underside 312 of each nose pin 308 is shaped, for example by a turning operation, so as to match exactly the contours of the bore through the nose. There is thus intimate contact between the pin surface 312 and the bore.

What is claimed is:

1. An instrument for the insertion of an intraocular lens into an eye, which comprises a body portion, a nose portion forward of the body portion and having a lumen through which the lens is arranged to pass, and a plunger movable through the body portion and the nose portion, wherein the nose portion is hingedly connected to the body portion and is movable between open and closed positions in the manner of the opening and closing of a shotgun barrel for the receipt of an intraocular lens therein in the open position.

2. An instrument according to claim 1, in which the nose portion can be locked into place in the closed position.

3. An instrument according to claim 1, in which the nose portion is pivotally mounted on a forward extension of the body portion, so that the hinge position is forward of the body portion and so that the nose portion, when in the open position, is spaced from the body portion to facilitate the placement of a lens into position in the nose portion.

4. An instrument according to claim 1, in which the lumen through the nose portion reduces in cross-section in a smoothly continuous manner so that as the lens passes deeper into the nose portion it is constrained to fold for dispensation through the tip of the nose portion.

5. An instrument according to claim 1, in which there is provided in the nose portion support means for the lens which defines an undulating support surface for the lens.

6. An instrument according to claim 5, in which the support means comprises two parallel spaced nose pins whose surfaces define the undulating support surface for the lens.

7. An instrument according to claim 6, in which the nose pins are set directly into bores made in the material of the nose portion.

8. An instrument according to claim 6, in which the nose pins are carried by a support member fixed into the rear of the nose portion, with the upper surfaces of the pins being proud of the surface of the support member, and with the undersides of the pins matching the contours of the lumen and being in contact therewith.

9. An instrument according to claim 1, which includes a cross pin extending transversely across the path of the lens and beneath which the lens is arranged to pass.

10. An instrument according to claim 9 in which there is provided in the nose portion support means for the lens comprising two parallel spaced nose pins whose surfaces define an undulating support surface for the lens, and in which the cross pin straddles the nose pins.

11. An instrument according to claim 1, in which the nose portion includes a viewing window for the lens.

12. An instrument according to claim 1, which is made from titanium or a titanium alloy.

* * * * *